United States Patent [19]

Anderson

[11] Patent Number: 4,873,341
[45] Date of Patent: Oct. 10, 1989

[54] WHITE BIS-IMIDE FLAME RETARDANTS

[75] Inventor: Keith G. Anderson, Baton Rouge, La.

[73] Assignee: Ethyl Corporation, Richmond, Va.

[21] Appl. No.: 246,209

[22] Filed: Sep. 19, 1988

[51] Int. Cl.$^4$ ........................................... C07D 209/48
[52] U.S. Cl. .................................................... 548/462
[58] Field of Search ........................................ 548/462

[56] References Cited

U.S. PATENT DOCUMENTS

| | | |
|---|---|---|
| 4,092,345 | 5/1978 | Wolford et al. ............ 548/462 |
| 4,125,535 | 11/1978 | Wolford ..................... 548/462 |
| 4,374,220 | 2/1983 | Sonnenberg ................ 548/462 |

Primary Examiner—Mary E. Ceperley
Attorney, Agent, or Firm—Edgar E. Spielman, Jr.

[57] ABSTRACT

This invention relates to a method for preparing a white or at least near-white product which is predominant in alkylene($C_1$–$C_5$)-bis-(tetrabromophthalimide). This method comprises: forming a solution which contains, as a solvent, (i) $SO_3$ or fuming sulfuric acid, and (ii) a haloalkane of the formula $RX_n$, wherein R is an alkyl group containing up to two carbon atoms, X is a halogen selected independently from Br and Cl, and n is 2 or 3 when R is an alkyl containing 1 carbon atom and is 1, 2 or 3 when R is an alkyl group containing 2 carbon atoms, and, as a solute, the yellow alkylene($C_1$–$C_5$)-bis-tetrabromophthalimide predominant product obtained from the reaction of tetrabromophthalic anhydride and diaminoalkane is the presence of water and alkanoic acid; and adding water to said solution to precipitate therefrom the white or at least near-white product.

14 Claims, No Drawings

WHITE BIS-IMIDE FLAME RETARDANTS

BACKGROUND OF THE INVENTION

This invention relates to a process for producing halogenated bis-imide flame retardant products having good color.

As is taught in U.S. Pat. No. 4,374,220, there are a multitude of halogenated bis-imides which are effective as flame retardants in composition with macromolecular flammable materials, e.g. polymers. These compositions are useful in making articles such as wire insulation and electronic housings. Of these halogenated bis-imides, the alkylene($C_1$–$C_5$)-bis-(tetrabromophthalimide)s are especially commercially significant.

A presently used commercial route for producing products predominant in alkylene($C_1$–$C_5$)-bis-(tetrabromophthalimide)s comprises reacting tetrabromophthalic anhydride with a diaminoalkane in the presence of water and an alkanoic acid to yield a reaction mass containing the intermediate, alkylene-diammonium-bis-(tetrabromophthalate). The reaction mass is then heated to about 210° C. for a period of about 8 hours to yield the desired alkylene($C_1$–$C_5$)-bis-(tetrabromophthalimide) predominant product which is then recovered therefrom. This product is particularly useful as it has good thermal stability and resistance to UV degradation. However, the product has a yellow color which argues against its presence in compositions used for forming white articles. Also, the intensity of the yellow color can vary between product batches, which color variance makes it difficult for the article manufacturer to maintain consistency in the color of the articles produced.

It is therefore an object of this invention to provide a method for producing a white or at least near-white alkylene($C_1$–$C_5$)-bis-(tetrabromophthalimide) predominant product from a likewise predominant yellow product produced by the reaction of tetrabromophthalic anhydride and diaminoalkane in the presence of water and alkanoic acid.

The Invention

The method of this invention comprises: forming a solution which contains, as a solvent, (i) $SO_3$ or fuming sulfuric acid, and (ii) a haloalkane of the formula $RX_n$, wherein R is an alkyl group containing up to two carbon atoms, X is a halogen selected independently from Br and Cl, and n is 2 or 3 when R is an alkyl containing 1 carbon atom and is 1, 2 or 3 when R is an alkyl group containing 2 carbon atoms, and, as a solute, the yellow alkylene($C_1$–$C_5$)-bis-(tetrabromophthalimide) predominant product obtained from the reaction of tetrabromophthalic anhydride and diaminoalkane in the presence of water and alkanoic acid; and adding water to said solution to precipitate therefrom a white or at least near-white product which is predominant in alkylene($C_1$–$C_5$)-bis-(tetrabromophthalimide).

For the purposes of this invention, the alkylene($C_1$–$C_5$)-bis-(tetrabromophthalimide)s referred to herein can be represented by the formula,

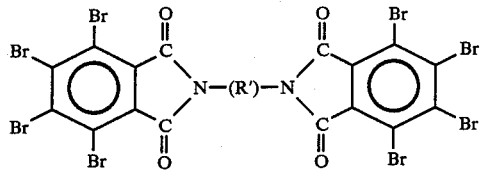

wherein R' is an alkylene radical containing 1 to 5 carbon atoms, e.g. methylene, ethylene, butylene, etc. Further, the yellow alkylene($C_1$–$C_5$)-bis-(tetrabromophthalimide) predominant product which is obtained from the reaction of tetrabromophthalic anhydride and diaminoalkane in the presence of water and an alkanoic acid will hereinafter be simply referred to as yellow product.

The yellow product and its production are well known and are described in U.S. Pat. No. 4,092,345, which is incorporated herein as if fully set forth. Example I of this patent illustrates the production of a yellow N,N',-1,2-ethylene-bis-(tetrabromophthalimide) predominant product. Besides acetic acid, it has been found that propionic acid is a highly suitable alkanoic acid for use in the Example I process. The yellow product can also be purchased from Ethyl Corporation as Saytex ® BT-93 flame retardant.

Due to safety considerations and to its ease in handling, fuming sulfuric acid is preferred over $SO_3$ as a solvent constituent of the solution. The fuming sulfuric acid will generally have from about a 10% to about 65% sulfur trioxide ($SO_3$) content. Preferred fuming sulfuric acids are those having an $SO_3$ content within the range of from about 30% to about 65% as such acids are readily available.

The amount of $SO_3$ or fuming sulfuric acid used is that amount which is necessary to dissolve the yellow product. Generally, the minimum amount needed is that amount which provides at least 8 mol of $SO_3$ per 1 mol of alkylene($C_1$–$C_5$)-bis-(tetrabromophthalide) in the yellow product. For example, for fuming sulfuric acid having an $SO_3$ content of about 65% $SO_3$, a minimum of 1 kg of the acid are used per kg of yellow product. Amounts in excess of the minimum amounts are prefered as complete dissolution does not then become a critical control factor for the processer. Excesses from about 100% to about 900% of the minimum are suitable. Larger excesses may be used but may adversely effect process economics.

Examples of haloalkanes which are suitable for the method of this invention are methylene bromide, methylene bromochloride, methylene chloride, chloroform, bromoform, chlorodibromomethane, dichlorobromomethane, dichloroethane, dibromoethane, 1,2-dichloro-1-bromoethane, 1-bromo-2-chloroethane and the like. The most preferred haloalkane is methylene chloride.

The amount of haloalkane used should be that amount which provides from about 1 to about 10 L of haloalkane per kg of yellow product. Preferred amounts are within the range of from about 5 to about 7 L of haloalkane per kg of yellow product. Amounts in excess of the highest amount recited above can be used. However, use of unnecessarily large amounts can adversely effect process economics.

The haloalkane is preferably washed with fuming sulfuric acid prior to its use in the solution so as to remove any oxidizable impurities therefrom. These oxidizable impurities, if not removed, could adversely effect the color of the final product. Should the haloalkane be found not to contain such impurities, such washing would not be necessary.

To form the solution, the yellow product, the $SO_3$ or fuming sulfuric acid and the haloalkane can be added one to the other in any order. It is preferred, however, to first form a solution of the yellow product and the $SO_3$ or fuming sulfuric acid and to then add the haloalkane thereto.

Irrespective of the order of addition, the dissolution of the yellow product will take some time, say at least 3 hrs, due to slow dissolution kinetics. To shorten the dissolution time, stirring or mixing can be effected. Also, the temperature during dissolution can be elevated to be within the range of from about 30° C. to about 130° C., depending on the strength of the fuming sulfuric acid. When dissolution occurs within this temperature range, the dissolution time generally will be within the range of from about 0.5 hr to about 2 hrs.

Water is added to the solution to effect the precipitation of a white or at least nearly-white product which is predominantly alkylene($C_1$–$C_5$)-bis-(tetrabromophthalimide). To obtain a high yield of product, the amount of water added is preferably that amount which maximizes precipitation of the alkylene($C_1$–$C_5$)-bis-(tetrabromophthalimide) originally in the solution. A simple procedure for determining the amount of water needed is to continue to add water as long as precipitate is being newly formed. Generally, the minimum amount of water added will be at least 1 mol of water per mol of $SO_3$ in the solution. Amounts which provide from about 0% to about 10% in excess of the minimum amount are preferred as such amounts insure maximum precipitation.

The water is added to the solution at a rate which will not cause excessive heat of solution or explosion. Also, the rate of water addition should not be so fast that the precipitation rate results in the occlusion of significant amounts of impurities in the crystals of the precipitate. Since the rate of water addition is dependent on several independent factors, e.g. vessel geometry, solution temperature, the particular haloalkane used, etc., observation and trial are best suited for determining the optimum rate of addition. Generally, it is preferred that the water be added to a stirred or agitated solution, that the water be added at several points into the solution, that the solution have a temperature between about 50° C. and about 130° C., and/or that the water addition rate be below about 1 mL/min per 1 L of solution.

After precipitation of the white product is complete, it can be separated from the solution by conventional techniques, e.g. filtration, centrifugation, etc.

The separated product is preferably washed with alcohol and water several times to reduce the amount of impurities remaining and to adjust the product's acid number to at least below 1. The washed product can then be dried conventionally.

Besides producing a white or at least nearly-white product, the method of the invention also yields a product which has good UV stability. Indeed, a $\Delta E_{48}$, Sunlighter, value of less than 2 is characteristic of formulations containing poly(butyleneterephthalate) and a N,N,-1,2-ethylene-bis-(tetrabromophthalimide) predominant product of the invention.

The alkylene($C_1$–$C_5$)-bis-(tetrabromophthalimide) constituent of the yellow product and the resultant white or at least nearly-white product of this invention are, of course, identical. Exemplary of these bisimides are N,N'-1,2-ethylene-bis-(tetrabromophthalimide), N,N'-methylene-bis-(tetrabromophthalimide), N,N'-1,4-butylene-bis-(tetrabromophthalimide), and N,N'-1,5-pentylene-bis-(tetrabromophthalimide). N,N'-1,2-ethylene-bis-(tetrabromophthalimide) is preferred. For both the yellow and white or at least near-white products, the term "predominant" means that each of the respective products contain at least 95 wt% alkylene($C_1$–$C_5$)-bis-(tetrabromophthalimide).

The yellow product, which is subjected to the method of this invention, contains certain impurities which contribute to its color. The identity of these impurities is not known precisely due to the extremely low solubility of the yellow product in solvents which prevents analysis.

The yellow product used in the method of this invention has a Hunter Colorimeter Yellowness Index of at least about 30.

The white or near white alkylene($C_1$–$C_5$)-bis-(tetrabromophthalimide) product produced by the method of this invention has a Hunter Colorimeter Yellowness Index less than 10.

The process equipment used in the method of this invention must be resistant to attack by the various reagents used so that color causing impurities from the equipment are not introduced into the final product. Therefore, the equipment, by way of example, should be glass-lined, 316-Stainless Steel, Hastelloy C, polytetrafluoroethylene-lined, or a combination of such.

The method of this invention can be run under any suitable pressure, the pressure not being critical. Atmospheric pressure is preferred.

EXAMPLE I

To a 1-L round-bottom flask equipped with a reflux condenser and stirrer charged 60.03g of Saytex® BT-93 flame retardant and 280 mL of 65% fuming sulfuric acid. The flask contents were stirred and heated to 55° C. After about 3 hrs, no solids were noticed in the flask. The resultant solution was cooled to a temperature of about 30° C. Methylene chloride (400 mL), that had been washed with fuming sulfuric acid, was then added to the flask. The flask contents were stirred until a clear, singlephase solution was obtained. To this solution was added water (90 mL) at a rate of 0.32 mL/min. A white precipitate was noted. The precipitate was recovered by filtering and weighed. The yield was 75% based upon the amount of Saytex® BT-93 flame retardant originally added. The precipitate was predominant in N,N'-1,2-ethylene-bis-(tetrabromophthalimide) and had a melting point of about 451° C. and had a Hunter Colorimeter Yellowness Index of 6.57.

EXAMPLE II

Example I was repeated with 60.07g of Saytex® BT-93 flame retardant and 400 mL of fuming sulfuric acid-washed methylene chloride. No fuming sulfuric acid was used as a solvent in the treatment of Saytex® BT-93 flame retardant. A yellow product was obtained.

EXAMPLE III

Example I was repeated with about 20 g of Saytex® BT-93 flame retardant, 70 mL of 65% fuming sulfuric acid, and 100 mL of oleum-washed methylene chloride washed with fuming sulfuric acid. 17 g of white product were obtained.

EXAMPLE IV

Example I was repeated with 60 g of Saytex ® BT-93 flame retardant and 310 mL of 65% fuming sulfuric acid. No methylene chloride was used. A yellow product was obtained.

EXAMPLE V

Product from Example III was compounded into Valox ® 315 poly(butyleneterephthalate) by Brabender mixer at the following composition: 10% white product; 5% $Sb_2O_3$; 85% Valox ®315. The resulting material was compression molded to form a plaque having a Hunter Colorimeter Yellowness index of 8.3 and a $\Delta E_{48}$, Sunlighter, of 1.45 upon exposure to UV-light. Valox ® 315 is available from General Electric Company.

EXAMPLE VI

Example V was repeated except that Saytex ® BT-93 flame retardant was used in place of the white product. The resulting plaque had a Hunter Colorimeter Yellowness index of 27 and a $\Delta E_{48}$, Sunlighter, of 1.73 upon exposure to UV-light.

What is claimed:

1. A method for producing a white or at least near-white product which predominantly contains alkylene($C_1$–$C_5$)-bis-(tetrabromophthalimide), which product is produced from the yellow product produced by the reaction of tetrabromophthalic anhydride and diaminoalkane in the presence of water and an alkanoic acid, said method comprising:
   (a) forming a solution which contains, as a solvent,
      (i) $SO_3$ or fuming sulfuric acid, and
      (ii) a haloalkane of the formula $RX_n$, wherein R is an alkyl group containing up to two carbon atoms, X is a halogen selected independently from Br and Cl, and n is 2 or 3 when R is an alkyl containing 1 carbon atom and is 1, 2 or 3 when R is an alkyl group containing 2 carbon atoms, and, as a solute, said yellow product, and
   (b) adding water to said solution to precipitate therefrom said white or at least near-white product.

2. The method of claim 1 wherein said alkylene($C_1$–$C_5$)-bis-(tetrabromophthalimide) is N,N'-1,2-ethylene-bis-(tetrabromophthalimide).

3. The method of claim 1 wherein said fuming sulfuric acid is used in forming said solution.

4. The method of claim 3 wherein said fuming sulfuric acid contains from about 10 to about 60 wt % $SO_3$.

5. The method of claim 1 wherein $RX_n$ is methylene chloride, methylene bromochloride, methylene bromide or a mixture comprised of any two or three of the foregoing haloalkanes.

6. The method of claim 1 wherein the amount of said haloalkane in said solution is within the range of from about 1 L to about 10 L per kg of dissolved yellow product.

7. The method of claim 1 wherein said alkylene($C_1$–$C_5$)-bis-(tetrabromophthalimide) is N,N'-1,2-ethylene-bis-(tetrabromophthalimide), said fuming sulfuric acid is used in forming said solution, said haloalkane is methylene chloride, and the amount of said haloalkane in said solution is within the range of from about 1 L to about 10 L per kg of dissolved yellow product.

8. The method of claim 1 wherein said solution is prepared by first dissolving said yellow product in said $SO_3$ or fuming sulfuric acid to form an intermediate solution and then adding to said intermediate solution said haloalkane.

9. The method of claim 8 wherein said alkylene($C_1$–$C_5$)-bis-(tetrabromophthalimide) is N,N'-1,2-ethylene-bis-(tetrabromophthalimide).

10. The method of claim 8 wherein said fuming sulfuric acid is used in forming said intermediate solution.

11. The method of claim 10 wherein said fuming sulfuric acid contains from about 10 to about 65 wt % $SO_3$.

12. The method of claim 8 wherein $RX_n$ is methylene chloride, methylene bromochloride, methylene bromide or a mixture comprised of any two or three of the foregoing haloalkanes.

13. The method of claim 8 wherein the amount of said haloalkane added to said intermediate solution is within the range of from about 1 L to about 10 L per kg of dissolved yellow product.

14. The method of claim 8 wherein said alkylene($C_1$–$C_5$)-bis-(tetrabromophthalimide) is N,N'-1,2-ethylene-bis-(tetrabromophthalimide), said fuming sulfuric acid is used in forming said intermediate solution, said haloalkane is methylene chloride, and the amount of said haloalkane added to said intermediate solution is within the range of from about 1 L to about 10 L per kg of dissolved yellow product.

* * * * *